US009247241B2

(12) United States Patent
Wong et al.

(10) Patent No.: US 9,247,241 B2
(45) Date of Patent: Jan. 26, 2016

(54) METHOD AND APPARATUS FOR DETECTION OF CARIES

(71) Applicant: Carestream Health, Inc., Rochester, NY (US)

(72) Inventors: Victor C. Wong, Rochester, NY (US); Rongguang Liang, Tucson, AZ (US); Donna K. Rankin-Parobek, Honeoye Falls, NY (US)

(73) Assignee: Carestream Health, Inc., Rochester, NY (US)

( * ) Notice: Subject to any disclaimer, the term of this patent is extended or adjusted under 35 U.S.C. 154(b) by 180 days.

(21) Appl. No.: 13/686,081

(22) Filed: Nov. 27, 2012

(65) Prior Publication Data

US 2013/0083181 A1   Apr. 4, 2013

Related U.S. Application Data

(60) Continuation of application No. 13/117,724, filed on May 27, 2011, now Pat. No. 8,345,942, and a division of application No. 12/541,329, filed on Aug. 14, 2009, now Pat. No. 7,974,453, and a division of application No. 11/262,869, filed on Oct. 31, 2005, now Pat. No. 7,596,253.

(51) Int. Cl.
  *G06K 9/00* (2006.01)
  *H04N 17/00* (2006.01)
  *A61B 5/00* (2006.01)

(52) U.S. Cl.
  CPC ............ *H04N 17/002* (2013.01); *A61B 5/0088* (2013.01)

(58) Field of Classification Search
  USPC ..................... 382/128, 294; 433/29
  See application file for complete search history.

(56) References Cited

U.S. PATENT DOCUMENTS

| 4,290,433 | A | 9/1981 | Alfano |
| 4,479,499 | A | 10/1984 | Alfano |
| 4,515,476 | A | 5/1985 | Ingmar |
| 6,038,024 | A | 3/2000 | Berner |
| 6,122,103 | A | 9/2000 | Perkins et al. |
| 6,231,338 | B1 | 5/2001 | de Josselin de Jong et al. |
| 6,519,037 | B2 * | 2/2003 | Jung et al. ................ 356/419 |
| 7,030,986 | B2 | 4/2006 | Overbeck et al. |

(Continued)

FOREIGN PATENT DOCUMENTS

| JP | S56-040137 A | 4/1981 |
| JP | H10-500588 | 1/1998 |

(Continued)

OTHER PUBLICATIONS

Fried et al.; "Imaging caries lesions and lesion progression with polarization sensitive optical coherence tomography" Journal of Biomedical Optics 7(4), Oct. 2002, pp. 618-627.

(Continued)

*Primary Examiner* — Wesley Tucker

(57) ABSTRACT

A method for obtaining an image of tooth tissue directs incident light toward a tooth, wherein the incident light excites a fluorescent emission from the tooth tissue. Fluorescence image data is obtained from the fluorescent emission. Back-scattered reflectance image data is obtained from back-scattered light from the tooth tissue. The fluorescence and back-scattered reflectance image data are combined to form an enhanced image of the tooth tissue for caries detection.

10 Claims, 8 Drawing Sheets

(56) References Cited

U.S. PATENT DOCUMENTS

| | | |
|---|---|---|
| 7,064,830 B2 | 6/2006 | Giorgianni et al. |
| 2002/0021439 A1 | 2/2002 | Priestley et al. |
| 2003/0156788 A1 | 8/2003 | Henning |
| 2004/0023184 A1 | 2/2004 | de Josselin de Jong et al. |
| 2004/0202356 A1 | 10/2004 | Stookey et al. |
| 2004/0236232 A1 | 11/2004 | Jonusauskas et al. |
| 2004/0240716 A1 | 12/2004 | de Josselin de Jong et al. |
| 2005/0003323 A1 | 1/2005 | Katsuda et al. |
| 2005/0032720 A1 | 2/2005 | Wingrove et al. |

FOREIGN PATENT DOCUMENTS

| | | |
|---|---|---|
| JP | 2002143080 | 5/2002 |
| JP | 2004-237081 | 8/2004 |
| JP | 2004-526550 | 9/2004 |
| JP | 2005-069807 A | 3/2005 |
| JP | 2005-304600 | 11/2005 |
| JP | 2005-319116 A | 11/2005 |
| JP | 2008-522761 | 7/2008 |
| WO | WO 95/26673 | 10/1995 |
| WO | WO 02/096281 | 12/2002 |
| WO | WO 03/005892 | 1/2003 |
| WO | WO 2005/002429 | 1/2005 |
| WO | WO 2006/063246 | 6/2006 |

OTHER PUBLICATIONS

WO2007/053293(A3)—PCT Search Report, dated Jun. 28, 2007 (6 pages).

* cited by examiner

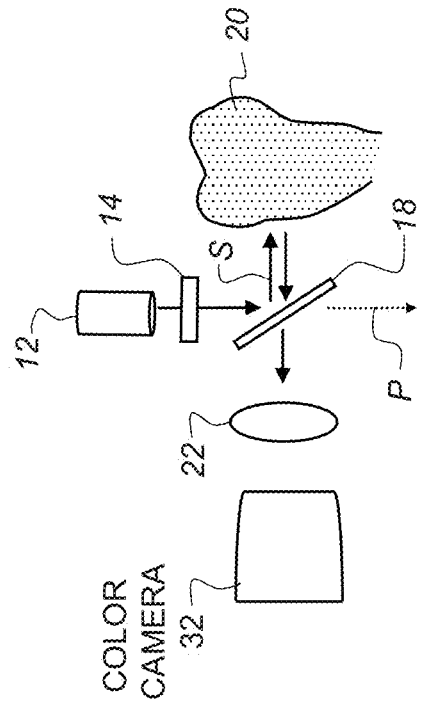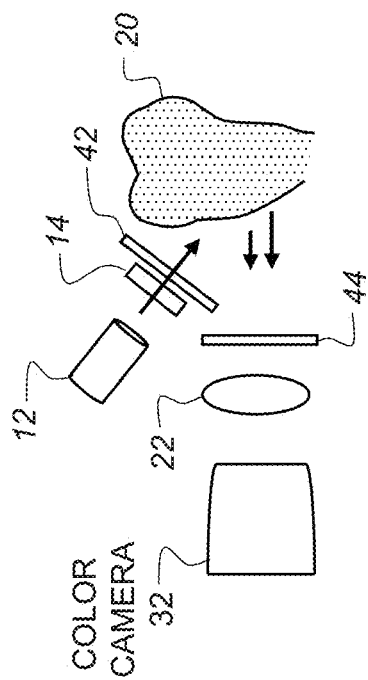

METHOD AND APPARATUS FOR DETECTION OF CARIES

CROSS REFERENCE TO RELATED APPLICATIONS

This is a Continuation of U.S. Ser. No. 13/117,724 entitled METHOD AND APPARATUS FOR DETECTION OF CARIES by Wong et al, filed on May 27, 2011, which was a Divisional of U.S. Ser. No. 12/541,329 entitled METHOD AND APPARATUS FOR DETECTION OF CARIES by Wong et al, filed on Aug. 14, 2009, (which issued as U.S. Pat. No. 7,974,453) which was a Divisional of U.S. Ser. No. 11/262,869 entitled METHOD AND APPARATUS FOR DETECTION OF CARIES by Wong et al, filed on Oct. 31, 2005 (which issued as U.S. Pat. No. 7,596,253).

FIELD OF THE INVENTION

This invention generally relates to a method and apparatus for dental imaging and more particularly to an improved method for early detection of caries using fluorescence and scattering of light.

BACKGROUND OF THE INVENTION

In spite of improvements in detection, treatment, and prevention techniques, dental caries remain a widely prevalent condition affecting people of all age groups. If not properly and promptly treated, caries can lead to permanent tooth damage and even to loss of teeth.

Traditional methods for caries detection include visual examination and tactile probing with a sharp dental explorer device, often assisted by radiographic (x-ray) imaging. Detection using these methods can be somewhat subjective, varying in accuracy due to many factors, including practitioner expertise, location of the infected site, extent of infection, viewing conditions, accuracy of x-ray equipment and processing, and other factors. There are also hazards associated with conventional detection techniques, including the risk of damaging weakened teeth and spreading infection with tactile methods as well as exposure to x-ray radiation. By the time caries are evident under visual and tactile examination, the disease is generally in an advanced stage, requiring a filling and, if not timely treated, possibly leading to tooth loss.

In response to the need for improved caries detection methods, there has been considerable interest in improved imaging techniques that do not employ x-rays. One method that has been commercialized employs fluorescence, caused when teeth are illuminated with high intensity blue light. This technique, termed quantitative light-induced fluorescence (QLF), operates on the principle that sound, healthy tooth enamel yields a higher intensity of fluorescence under excitation from some wavelengths than does de-mineralized enamel that has been damaged by caries infection. The strong correlation between mineral loss and loss of fluorescence for blue light excitation is then used to identify and assess carious areas of the tooth. A different relationship has been found for red light excitation, a region of the spectrum for which bacteria and bacterial by-products in carious regions absorb and fluoresce more pronouncedly than do healthy areas.

Among proposed solutions for optical detection of caries are the following:

U.S. Pat. No. 4,515,476 (Ingmar) discloses use of a laser for providing excitation energy that generates fluorescence at some other wavelength for locating carious areas.

U.S. Pat. No. 6,231,338 (de Josselin de Jong et al.) discloses an imaging apparatus for identifying dental caries using fluorescence detection.

U.S. Patent Application Publication No. 2004/0240716 (de Josselin de Jong et al.) discloses methods for improved image analysis for images obtained from fluorescing tissue.

U.S. Pat. No. 4,479,499 (Alfano) describes a method for using transillumination to detect caries based on the translucent properties of tooth structure.

Among commercialized products for dental imaging using fluorescence behavior is the QLF Clinical System from Inspektor Research Systems BV, Amsterdam, The Netherlands. Using a different approach, the Diagnodent Laser Caries Detection Aid from KaVo Dental Corporation, Lake Zurich, Ill., detects caries activity monitoring the intensity of fluorescence of bacterial by-products under illumination from red light.

U.S. Patent Application Publication No. 2004/0202356 (Stookey et al.) describes mathematical processing of spectral changes in fluorescence in order to detect caries in different stages with improved accuracy. Acknowledging the difficulty of early detection when using spectral fluorescence measurements, the '2356 Stookey et al. disclosure describes approaches for enhancing the spectral values obtained, effecting a transformation of the spectral data that is adapted to the spectral response of the camera that obtains the fluorescent image.

While the disclosed methods and apparatus show promise in providing non-invasive, non-ionizing imaging methods for caries detection, there is still room for improvement. One recognized drawback with existing techniques that employ fluorescence imaging relates to image contrast. The image provided by fluorescence generation techniques such as QLF can be difficult to assess due to relatively poor contrast between healthy and infected areas. As noted in the '2356 Stookey et al. disclosure, spectral and intensity changes for incipient caries can be very slight, making it difficult to differentiate non-diseased tooth surface irregularities from incipient caries.

Overall, it is well-recognized that, with fluorescence techniques, the image contrast that is obtained corresponds to the severity of the condition. Accurate identification of caries using these techniques often requires that the condition be at a more advanced stage, beyond incipient or early caries, because the difference in fluorescence between carious and sound tooth structure is very small for caries at an early stage. In such cases, detection accuracy using fluorescence techniques may not show marked improvement over conventional methods. Because of this shortcoming, the use of fluorescence effects appears to have some practical limits that prevent accurate diagnosis of incipient caries. As a result, a caries condition may continue undetected until it is more serious, requiring a filling, for example.

Detection of caries at very early stages is of particular interest for preventive dentistry. As noted earlier, conventional techniques generally fail to detect caries at a stage at which the condition can be reversed. As a general rule of thumb, incipient caries is a lesion that has not penetrated substantially into the tooth enamel. Where such a caries lesion is identified before it threatens the dentin portion of the tooth, remineralization can often be accomplished, reversing the early damage and preventing the need for a filling. More advanced caries, however, grows increasingly more difficult to treat, most often requiring some type of filling or other type of intervention.

In order to take advantage of opportunities for non-invasive dental techniques to forestall caries, it is necessary that caries be detected at the onset. In many cases, as is acknowledged in the '2356 Stookey et al. disclosure, this level of detection has been found to be difficult to achieve using existing fluorescence imaging techniques, such as QLF. As a result, early caries can continue undetected, so that by the time positive detection is obtained, the opportunity for reversal using low-cost preventive measures can be lost.

Thus, it can be seen that there is a need for a non-invasive, non-ionizing imaging method for caries detection that offers improved accuracy for detection of caries, particularly in its earlier stages.

SUMMARY OF THE INVENTION

The present invention provides a method for obtaining an image of tooth tissue comprising: (a) directing incident light toward a tooth, wherein the incident light excites a fluorescent emission from the tooth tissue; (b) obtaining fluorescence image data from the fluorescent emission; (c) obtaining, from back-scattered light, back-scattered reflectance image data from the tooth tissue; and d) combining the fluorescence and back-scattered reflectance image data to form an enhanced image of the tooth tissue.

It is a feature of the present invention that it utilizes both fluorescence and reflectance image data for dental imaging.

It is an advantage of the present invention that it offers enhancement over existing fluorescence imaging techniques, useful for detection of caries in its incipient stages.

These and other objects, features, and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings.

FIG. 4A is a schematic block diagram of an imaging apparatus for caries detection according to an alternate embodiment using polarized light.

FIG. 4B is a schematic block diagram of an imaging apparatus for caries detection according to an alternate embodiment using a polarizing beamsplitter to provide polarized light and to minimize specular reflection.

DETAILED DESCRIPTION OF THE INVENTION

Figure 1:
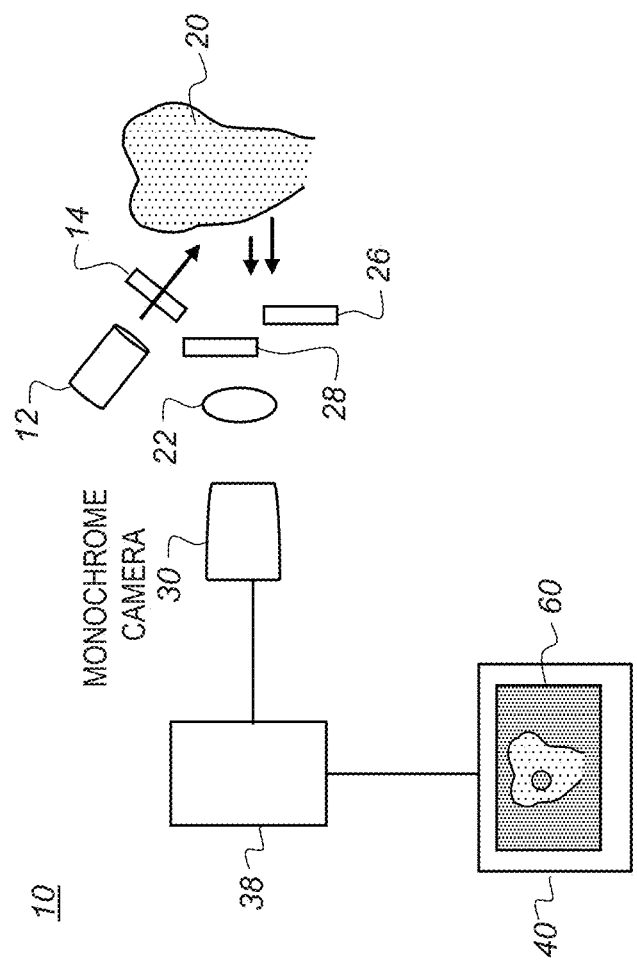
FIG. 1 is a schematic block diagram of an imaging apparatus for caries detection according to one embodiment.

The present description is directed in particular to elements forming part of, or cooperating more directly with, apparatus in accordance with the invention. It is to be understood that elements not specifically shown or described may take various forms well known to those skilled in the art.

As noted in the preceding background section, it is known that fluorescence can be used to detect dental caries using either of two characteristic responses: First, excitation by a blue light source causes healthy tooth tissue to fluoresce in the green spectrum. Secondly, excitation by a red light source can cause bacterial by-products, such as those indicating caries, to fluoresce in the red spectrum.

In order for an understanding of how light is used in the present invention, it is important to give more precise definition to the terms "reflectance" and "back-scattering" as they are used in biomedical applications in general and, more particularly, in the method and apparatus of the present invention. In broadest optical terminology, reflectance generally denotes the sum total of both specular reflectance and scattered reflectance. (Specular reflection is that component of the excitation light that is reflected by the tooth surface at the same angle as the incident angle.) In many biomedical applications, however, as in the dental application of the present invention, the specular component of reflectance is of no interest and is, instead, generally detrimental to obtaining an image or measurement from a sample. The component of reflectance that is of interest for the present application is from back-scattered light only. Specular reflectance must be blocked or otherwise removed from the imaging path. With this distinction in mind, the term "back-scattered reflectance" is used in the present application to denote the component of reflectance that is of interest. "Back-scattered reflectance" is defined as that component of the excitation light that is elastically back-scattered over a wide range of angles by the illuminated tooth structure. "Reflectance image" data, as this term is used in the present invention, refers to image data obtained from back-scattered reflectance only, since specular reflectance is blocked or kept to a minimum. In the scientific literature, back-scattered reflectance may also be referred to as back-reflectance or simply as back-scattering. Back-scattered reflectance is at the same wavelength as the excitation light.

It has been shown that light scattering properties differ between healthy and carious dental regions. In particular, reflectance of light from the illuminated area can be at measurably different levels for normal versus carious areas. This change in reflectance, taken alone, may not be sufficiently pronounced to be of diagnostic value when considered by itself, since this effect is very slight, although detectable. For more advanced stages of caries, for example, back-scattered reflectance may be less effective an indicator than at earlier stages.

In conventional fluorescence measurements such as those obtained using QLF techniques, reflectance itself is an effect that is avoided rather than utilized. A filter is usually employed to block off all excitation light from reaching the detection device. For this reason, the slight but perceptible change in back-scattered reflectance from excitation light has received little attention for diagnosing caries.

The inventors have found, however, that this back-scattered reflectance change can be used in conjunction with the fluorescent effects to more clearly and more accurately pinpoint a carious location. Moreover, the inventors have observed that the change in light scattering activity, while it can generally be detected wherever a caries condition exists, is more pronounced in areas of incipient caries. This back-scattered reflectance change is evident at early stages of caries, even when fluorescent effects are least pronounced.

The present invention takes advantage of the observed back-scattering behavior for incipient caries and uses this effect, in combination with fluorescence effects described previously in the background section, to provide an improved capability for dental imaging to detect caries. The inventive technique, hereafter referred to as fluorescence imaging with reflectance enhancement (FIRE), not only helps to increase the contrast of images over that of earlier approaches, but also makes it possible to detect incipient caries at stages where preventive measures are likely to effect remineralization, repairing damage done by the caries infection at a stage well before more complex restorative measures are necessary. Advantageously, FIRE detection can be accurate at an earlier stage of caries infection than has been exhibited using existing fluorescence approaches that measure fluorescence alone.

Imaging Apparatus

Referring to FIG. 1, there is shown an imaging apparatus 10 for caries detection using the FIRE method in one embodiment. A light source 12 directs an incident light, at a blue wavelength range or other suitable wavelength range, toward tooth 20 through an optional lens 14 or other light beam conditioning component. The tooth 20 may be illuminated at a proximal surface (as shown) or at an occlusal surface (not shown). Two components of light are then detected by a monochrome camera 30 through a lens 22: a back-scattered light component having the same wavelength as the incident light and having measurable reflectance; and a fluorescent light that has been excited due to the incident light. For FIRE imaging, specular reflection causes false positives and is undesirable. To minimize specular reflection pick up, the camera 30 is positioned at a suitable angle with respect to the light source 12. This allows imaging of back-scattered light without the confounding influence of a specularly reflected component.

In the embodiment of FIG. 1, monochrome camera 30 has color filters 26 and 28. One of color filters 26 and 28 is used during reflectance imaging, the other is used during fluorescence imaging. A processing apparatus 38 obtains and processes the reflectance and fluorescence image data and forms a FIRE image 60. FIRE image 60 is an enhanced diagnostic image that can be printed or can appear on a display 40. FIRE image 60 data can also be transmitted to storage or transmitted to another site for display.

Figure 2:
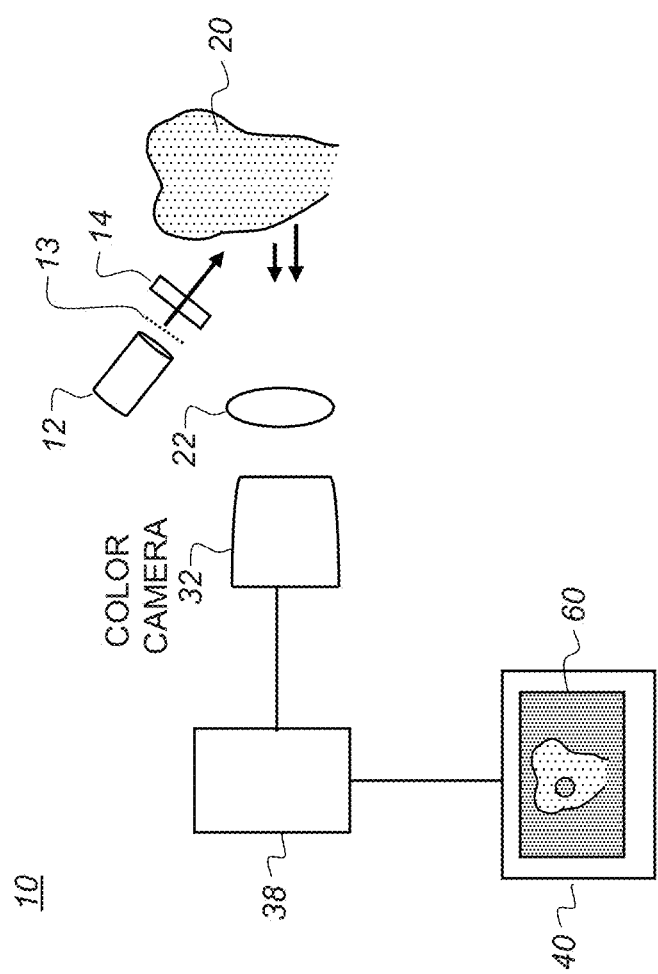
FIG. 2 is a schematic block diagram of an imaging apparatus for caries detection according to an alternate embodiment.

Referring to FIG. 2, there is shown an alternate embodiment using a color camera 32. With this arrangement, auxiliary filters would not generally be needed, since color camera 32 would be able to obtain the reflectance and fluorescence images from the color separations (also called color planes) of the full color image of tooth 20.

Light source 12 is typically centered around a blue wavelength, such as about 405 nm in one embodiment. In practice, light source 12 could emit light ranging in wavelength from an upper ultraviolet range to a deeper blue, between about 300 and 500 nm. Light source 12 can be a laser or could be fabricated using one or more light emitting diodes (LEDs). Alternately, a broadband source, such as a xenon lamp, having a supporting color filter for passing the desired wavelengths could be used. Lens 14 or other optical element may serve to condition the incident light, such as by controlling the uniformity and size of the illumination area. For example, a diffuser 13, shown as a dotted line in FIG. 2, might be used before or after lens 14 to smooth out the hot spots of an LED beam. The path of illumination light might include light guiding or light distributing structures such as optical fibers or a liquid light guide, for example (not shown). Light level is typically a few milliwatts in intensity, but can be more or less, depending on the light conditioning and sensing components used.

Figure 3:
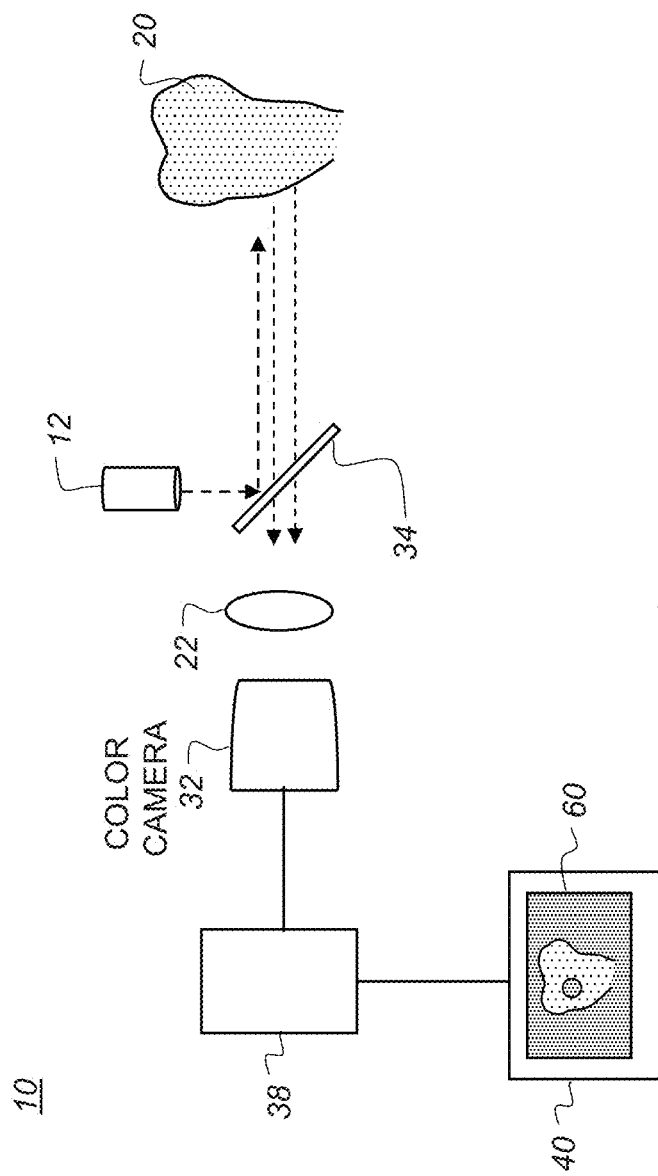
FIG. 3 is a schematic block diagram of an imaging apparatus for caries detection according to an alternate embodiment.

Referring to FIG. 3, the illumination arrangement could alternately direct light at normal incidence, turned through a beamsplitter 34. Camera 32 would then be disposed to obtain the image light that is transmitted through beamsplitter 34. Other options for illumination include multiple light sources directed at the tooth with angular incidence from one or more sides. Alternately, the illumination might use an annular ring or an arrangement of LED sources distributed about a center such as in a circular array to provide light uniformly from multiple angles. Illumination could also be provided through an optical fiber or fiber array.

The imaging optics, represented as lens 22 in FIGS. 1-3, could include any suitable arrangement of optical components, with possible configurations ranging from a single lens component to a multi-element lens. Clear imaging of the tooth surface, which is not flat but can have areas that are both smoothly contoured and highly ridged, requires that imaging optics have sufficient depth of focus. Preferably, for optimal resolution, the imaging optics provide an image size that substantially fills the sensor element of the camera. Telecentric optics are advantaged for lens 22, providing image-bearing light that is not highly dependent on ray angle.

Image capture can be performed by either monochrome camera 30 (FIG. 1) or color camera 32 (FIG. 2). Typically, camera 30 or 32 employs a CMOS or CCD image sensor. The monochrome version would typically employ a retractable spectral filter 26, 28 suitable for the wavelength of interest. For light source 12 having a blue wavelength, spectral filter 26 for capturing reflectance image data would transmit predominately blue light. Spectral filter 28 for capturing fluorescence image data would transmit light at a different wavelength, such as predominately green light. Preferably, spectral filters 26 and 28 are automatically switched into place to allow capture of both reflectance and fluorescence images in very close succession. Both images are obtained from the same position to allow accurate registration of the image data.

Spectral filter 28 would be optimized with a pass-band that captures fluorescence data over a range of suitable wavelengths. The fluorescent effect that has been obtained from tooth 20 can have a relative broad spectral distribution in the visible range, with light emitted that is outside the wavelength range of the light used for excitation. The fluorescent emission is typically between about 450 nm and 650 nm, while generally peaking in the green region, roughly from around 500 nm to about 600 nm. Thus a green light filter is generally preferred for spectral filter 28 in order to obtain this fluorescence image at its highest energy levels. However, other ranges of the visible spectrum could also be used in other embodiments.

In a similar manner, spectral filter 26 would be optimized with a pass-band that captures reflectance data over a wavelength range covering at least a significant portion of the spectral energy of the light source 12 used. For reasons previously discussed, a blue light filter is generally used for spectral filter 26 in order to obtain the reflectance image at its highest energy level.

Camera controls are suitably adjusted for obtaining each type of image. For example, when capturing the fluorescence image, it is necessary to make appropriate exposure adjustments for gain, shutter speed, and aperture, since this image may not be intense. When using color camera 32 (FIG. 2), color filtering is performed by the color filter arrays on the camera image sensor. The reflectance image is captured in the blue color plane; simultaneously, the fluorescence image is captured in the green color plane. That is, a single exposure captures both back-scattered reflectance and fluorescence images.

Processing apparatus 38 is typically a computer workstation but may, in its broadest application, be any type of control logic processing component or system that is capable of obtaining image data from camera 30 or 32 and executing image processing algorithms upon that data to generate the FIRE image 60 data. Processing apparatus 38 may be local or may connect to image sensing components over a networked interface.

Figure 5:
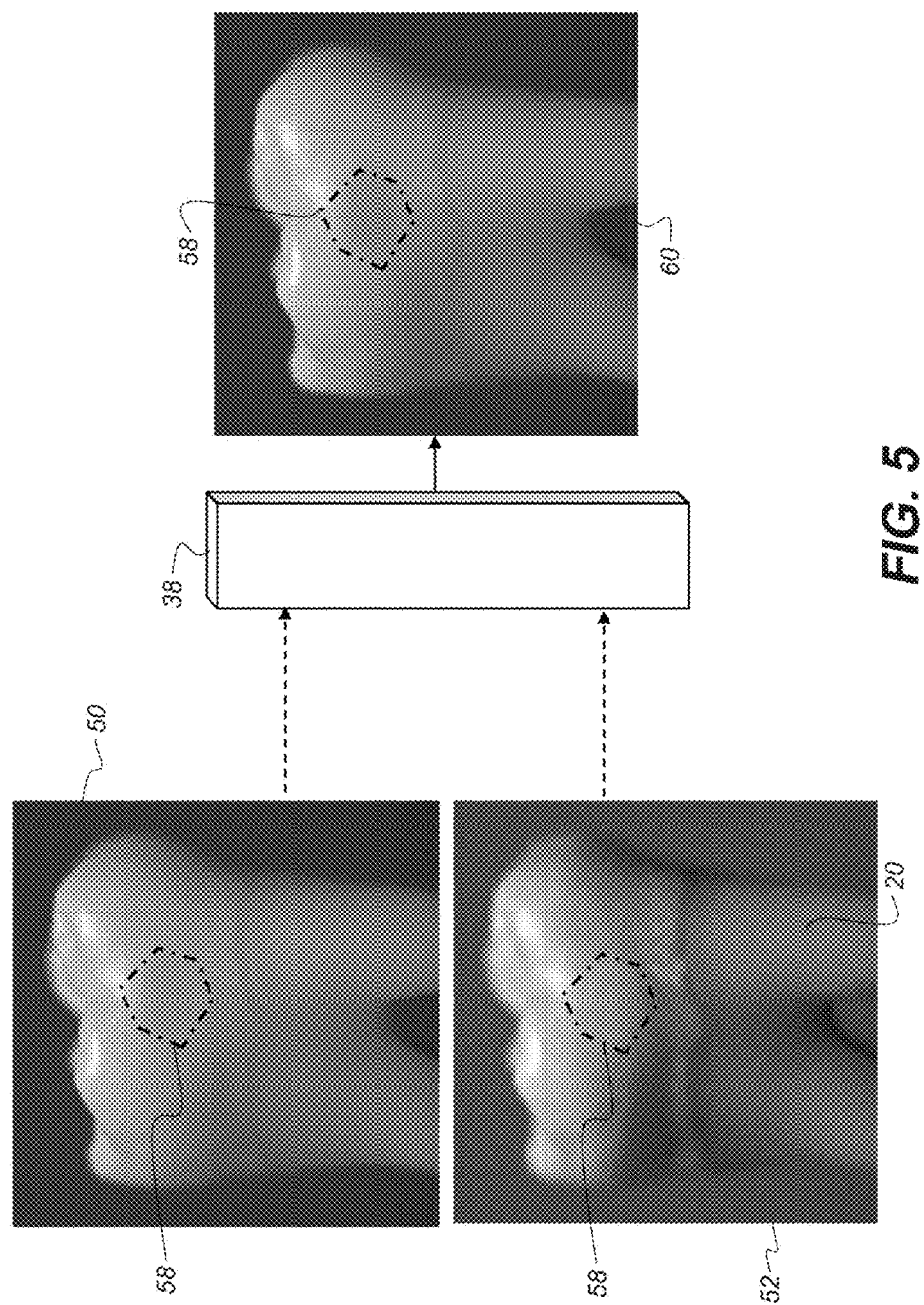
FIG. 5 is a view showing the process for combining dental image data to generate a fluorescence image with reflectance enhancement according to the present invention.

Referring to FIG. 5, there is shown, in schematic form, how the FIRE image 60 is formed according to the present invention. Two images of tooth 20 are obtained, a green fluorescence image 50 and a blue reflectance image 52. As noted earlier, it must be emphasized that the reflectance light used for reflectance image 52 and its data is from back-scattered reflectance, with specular reflectance blocked or kept as low as possible. In the example of FIG. 5, there is a carious region 58, represented in phantom outline in each of images 50, 52, and 60, that causes a slight decrease in fluorescence and a slight increase in reflectance. The carious region 58 may be imperceptible or barely perceptible in either fluorescence image 50 or reflectance image 52, taken individually. Processing apparatus 38 operates upon the image data using an image processing algorithm as discussed below for both images 50 and 52 and provides FIRE image 60 as a result. The contrast between carious region 58 and sound tooth structure is heightened, so that a caries condition is made more visible in FIRE image 60.

Figure 6:
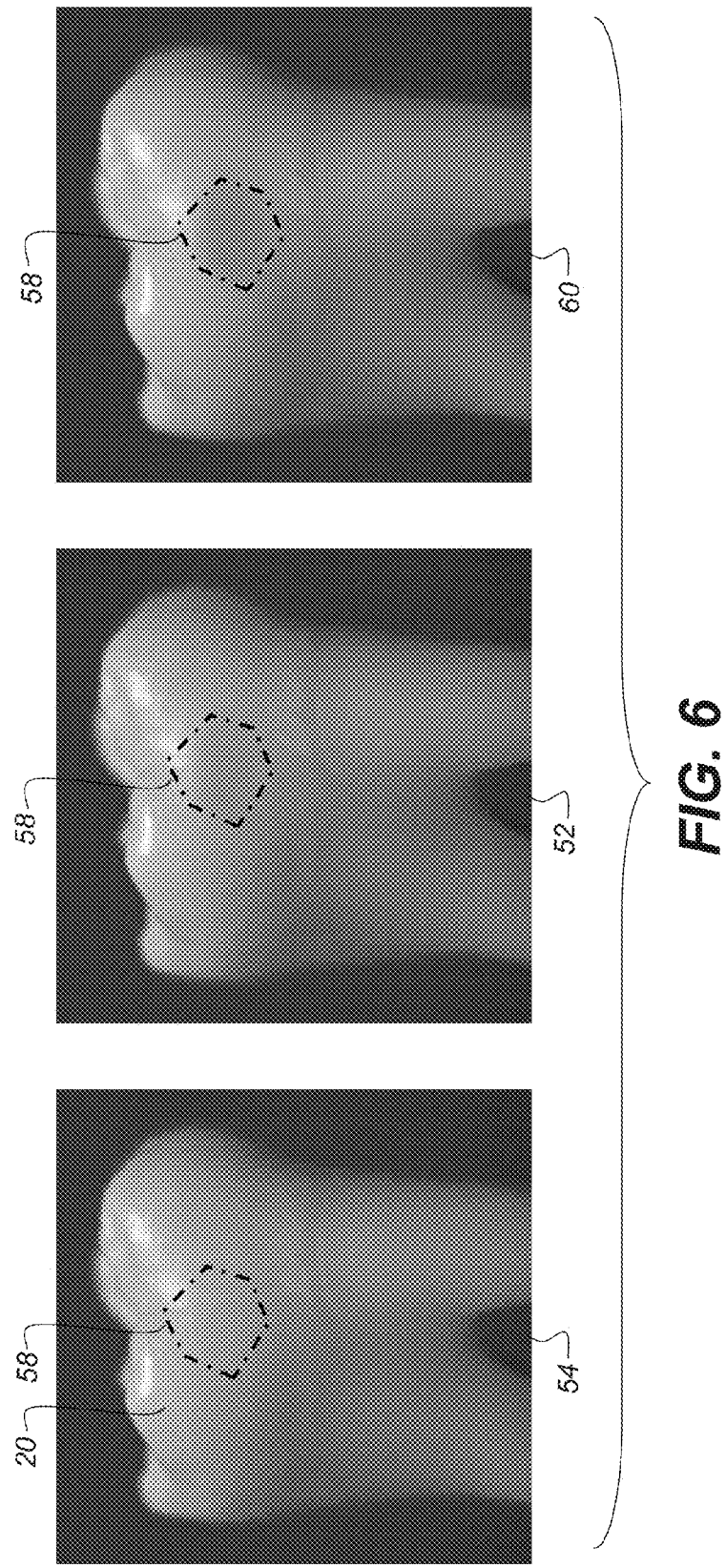
FIG. 6 is a composite view showing the contrast improvement of the present invention in a side-by-side comparison with conventional visual and fluorescence methods.

FIG. 6 shows the contrast improvement of the present invention in a side-by-side comparison with a visual white-light image 54 and conventional fluorescence methods. For caries at a very early stage, the carious region 58 may look indistinct from the surrounding healthy tooth structure in white-light image 54, either as perceived directly by eye or as captured by an intraoral camera. In the green fluorescence image 50 captured by existing fluorescence method, the carious region 58 may show up as a very faint, hardly noticeable shadow. In contrast, in the FIRE image 60 generated by the present invention, the same carious region 58 shows up as a darker, more detectable spot. Clearly, the FIRE image 60, with its contrast enhancement, offers greater diagnostic value.

Image Processing

As described earlier with reference to FIGS. 5 and 6, processing of the image data uses both the reflectance and fluorescence image data to generate a final image that can be used to identify carious areas of the tooth. There are a number of alternative processing methods for combining the reflectance and fluorescence image data to form FIRE image 60 for diagnosis. In one embodiment, this image processing performs the following operation for each pixel:

$$(m^*F_{value}) - (n^*R_{value}) \qquad (1)$$

where m and n are suitable multipliers (positive coefficients) and $F_{value}$ and $R_{value}$ are the code values obtained from fluorescence and reflectance image data, respectively.

Back-scattered reflectance is higher (brighter) for image pixels in the carious region, yielding a higher reflectance value $R_{value}$ for these pixels than for surrounding pixels. The fluorescence, meanwhile, is lower (darker) for image pixels in the carious region, yielding a lower fluorescence value $F_{value}$ for these pixels than for surrounding pixels. For a pixel in a carious region, the fluorescence is considerably weaker in intensity compared to the reflectance. After multiplying the fluorescence and reflectance by appropriate scalar multipliers m and n, respectively, where m>n, the scaled fluorescence values of all pixels are made to exceed or equal to the corresponding scaled reflectance values:

$$(m^*F_{value}) > \text{or} = (n^*R_{value}). \qquad (2)$$

Subtraction of the scaled back-scattered reflectance value from the scaled fluorescence value for each pixel then results in a processed image where the contrast between the intensity values for pixels in the carious region and pixels in sound region is accentuated, resulting in a contrast enhancement that can be readily displayed and recognized. In one embodiment, scalar multiplier n for reflectance value $R_{value}$ is one.

Figure 7:
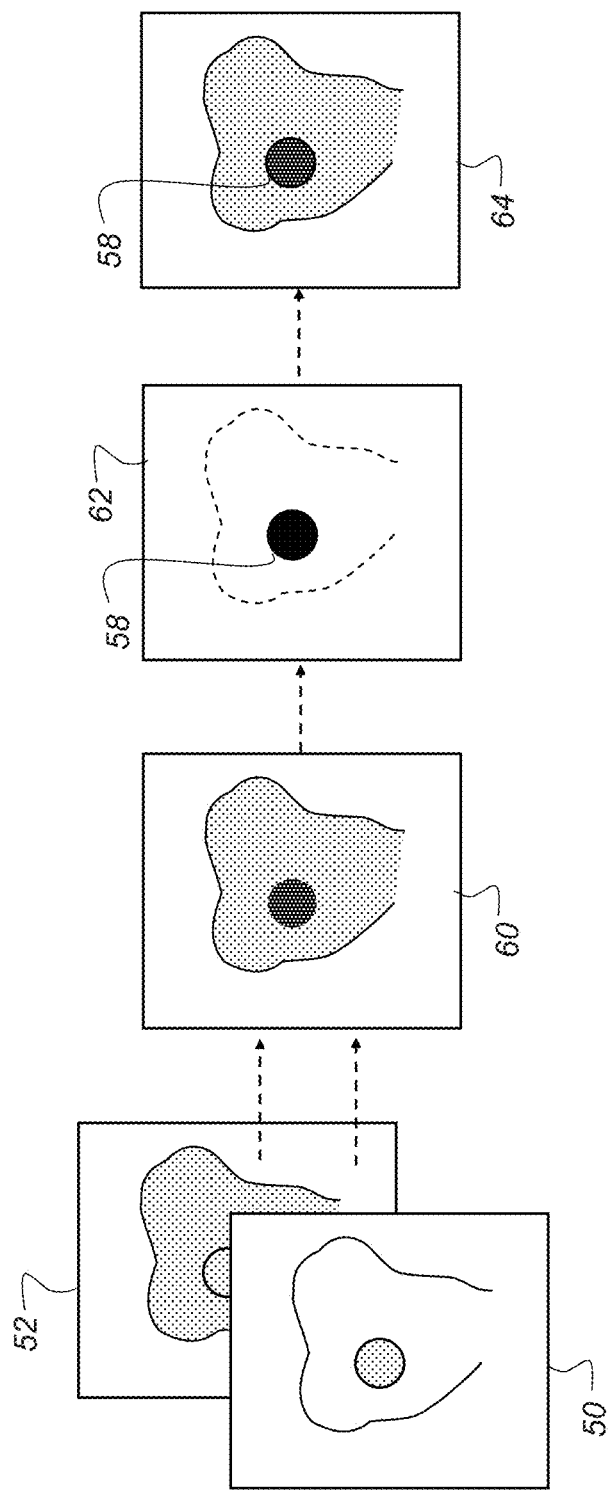
FIG. 7 is a block diagram showing a sequence of image processing for generating an enhanced threshold image according to one embodiment.

Following an initial combination of fluorescence and reflectance values as given earlier with reference to the example of expression (1), additional image processing may also be of benefit. A thresholding operation, executed using image processing techniques familiar to those skilled in the imaging arts, or some other suitable conditioning of the combined image data used for FIRE image 60, may be used to further enhance the contrast between a carious region and sound tooth structure. Referring to FIG. 7, there is shown, in block diagram form, a sequence of image processing for generating an enhanced threshold FIRE image 64 according to one embodiment. Fluorescence image 50 and reflectance image 52 are first combined to form FIRE image 60, as described previously. A thresholding operation is next performed, providing threshold image 62 that defines more clearly the area of interest, carious region 58. Then, threshold image 62 is combined with original FIRE image 60 to generate enhanced threshold FIRE image 64. Similarly, the results of threshold detection can also be superimposed onto a white light image 54 (FIG. 6) in order to definitively outline the location of a carious infection.

The choice of appropriate coefficients m and n is dependent on the spectral content of the light source and the spectral response of the image capture system. There is variability in the center wavelength and spectral bandwidth from one LED to the next, for example. Similarly, variability exits in the spectral responses of the color filters and image sensors of different image capture systems. Such variations affect the relative magnitudes of the measured reflectance and fluorescence values. Therefore, it may be necessary to determine a different m and n value for each imaging apparatus 10 as a part of an initial calibration process. A calibration procedure used during the manufacturing of imaging apparatus 10 can then optimize the m and n values to provide the best possible contrast enhancement in the FIRE image that is formed.

In one calibration sequence, a spectral measurement of the light source 12 used for reflectance imaging is obtained. Then, spectral measurement is made of the fluorescent emission that is excited from the tooth. This data provides a profile of the relative amount of light energy available over each wavelength range of interest. Then the spectral response of camera 30 (with appropriate filters) or 32 is quantified against a known reference. These data are then used, for example, to generate a set of optimized multiplier m and n values to be used by processing apparatus 38 of the particular imaging apparatus 10 for forming FIRE image 60.

It can be readily appreciated that any number of more complex image processing algorithms could alternately be used for combining the reflectance and fluorescence image data in order to obtain an enhanced image that identifies carious regions more clearly. It may be advantageous to apply a number of different imaging algorithms to the image data in order to obtain the most useful result. In one embodiment, an operator can elect to use any of a set of different image processing algorithms for conditioning the fluorescence and reflectance image data obtained. This would allow the operator to check the image data when processed in a number of different ways and may be helpful for optimizing the detection of carious lesions having different shape-related characteristics or that occur over different areas of the tooth surface.

It is emphasized that the image contrast enhancement achieved in the present invention, because it employs both reflectance and fluorescence data, is advantaged over conventional methods that use fluorescent image data only. Conventionally, where only fluorescence data is obtained, image processing has been employed to optimize the data, such as to transform fluorescence data based on spectral response of the camera or of camera filters or other suitable characteristics. For example, the method of the '2356 Stookey et al. disclosure, cited above, performs this type of optimization, transforming fluorescence image data based on camera response. However, these conventional approaches overlook the added advantage of additional image information that the back-scattered reflectance data obtains.

Alternate Embodiments

The method of the present invention admits a number of alternate embodiments. For example, the contrast of either or both of the reflectance and fluorescence images may be improved by the use of a polarizing element. It has been observed that enamel, having a highly structured composition, is sensitive to the polarization of incident light. Polarized light has been used to improve the sensitivity of dental imaging techniques, for example, in "Imaging Caries Lesions and Lesion Progression with Polarization Sensitive Optical Coherence Tomography" in *J. Biomed Opt., October* 2002; 7(4): pp. 618-27, by Fried et al.

Polarization control can also be advantageously employed as a means to minimize specular reflection. Specular reflection tends to preserve the polarization state of the incident light. For example, where the incident light is S-polarized, the specular reflected light is also S-polarized. Back-scattering, on the other hand, tends to de-polarize or randomize the polarization of the incident light. Where incident light is S-polarized, back-scattered light has both S- and P-polarization components. Using a polarizer and analyzer, this difference in polarization handling can be employed to help eliminate unwanted specular reflectance from the reflectance image, so that only back-scattered reflectance is obtained.

Referring to FIG. 4A, there is shown an embodiment of imaging apparatus 10 that employs a polarizer 42 in the path of illumination light. Polarizer 42 passes linearly polarized incident light. An analyzer 44 may be provided in the path of image-bearing light from tooth 20 as a means to minimize specular reflection component. With this polarizer 42/analyzer 44 combination as polarizing elements, reflectance light sensed by camera 30 or 32 is predominantly back-scattered light, that portion of the reflectance that is desirable for combination with the fluorescence image data according to the present invention. In the case where the illumination light from light source 12 is already linearly polarized, such as from a laser, polarizer 42 is not needed; analyzer 44 would then be oriented with its polarization axis orthogonal to the polarization direction of the illumination light for rejecting specular reflection.

An alternate embodiment, shown in FIG. 4B, employs a polarizing beamsplitter 18 (sometimes termed a polarization beamsplitter) as a polarizing element. In this arrangement, polarizing beamsplitter 18 advantageously performs the functions of both the polarizer and the analyzer for image-bearing light, thus offering a more compact solution. Tracing the path of illumination and image-bearing light shows how polarizing beamsplitter 18 performs this function. Polarization beamsplitter 18 transmits P-polarization, as shown by the dotted arrow in FIG. 4B, and reflects S-polarization, directing this light to tooth 20. Back-scattering by the tooth 20 structure depolarizes this light. Polarization beamsplitter 18 treats the back-scattered light in the same manner, transmitting the P-polarization and reflecting the S-polarization. The resulting P-polarized light can then be detected at camera 30 (with suitable filter as was described with reference to FIG. 1) or color camera 32. Because specularly reflected light is S-polarized, polarization beamsplitter 18 effectively removes this specular reflective component from the light that reaches camera 30, 32.

Polarized illumination results in further improvement in image contrast, but at the expense of light level, as can be seen from the description of FIGS. 4A and 4B. Hence, when using polarized light in this way, it may be necessary to employ a higher intensity light source 12. It is also of benefit to use polarizing elements having higher transmission over the wavelength of interest.

One type of polarizer 42 that has particular advantages for use in the present application is the wire grid polarizer, such as those available from Moxtek Inc. of Orem, Utah and described in U.S. Pat. No. 6,122,103 (Perkins et al.) The wire grid polarizer exhibits good angular and color response, with relatively good transmission over the blue spectral range. Either or both polarizer 42 and analyzer 44 in the configuration of FIG. 4A could be wire grid polarizers. Wire grid polarizing beamsplitters are also available, and can be used in the configuration of FIG. 4B.

The method of the present invention takes advantage of the way the tooth tissue responds to incident light of sufficient intensity, using the combination of fluorescence and light reflectance to indicate carious areas of the tooth with improved accuracy and clarity. In this way, the present invention offers an improvement upon existing non-invasive fluorescence detection techniques for caries. As was described in the background section given above, images that have been obtained using fluorescence only may not clearly show caries due to low contrast. The method of the present invention provides images having improved contrast and is, therefore, of more potential benefit to the diagnostician for identifying caries.

In addition, unlike earlier approaches using fluorescence alone, the method of the present invention also provides images that can be used to detect caries in its very early incipient stages. This added capability, made possible because of the perceptible back-scattering effects for very early carious lesions, extends the usefulness of the fluorescence technique and helps in detecting caries during its reversible stages, so that fillings or other restorative strategies might not be needed.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention.

Figure 8:
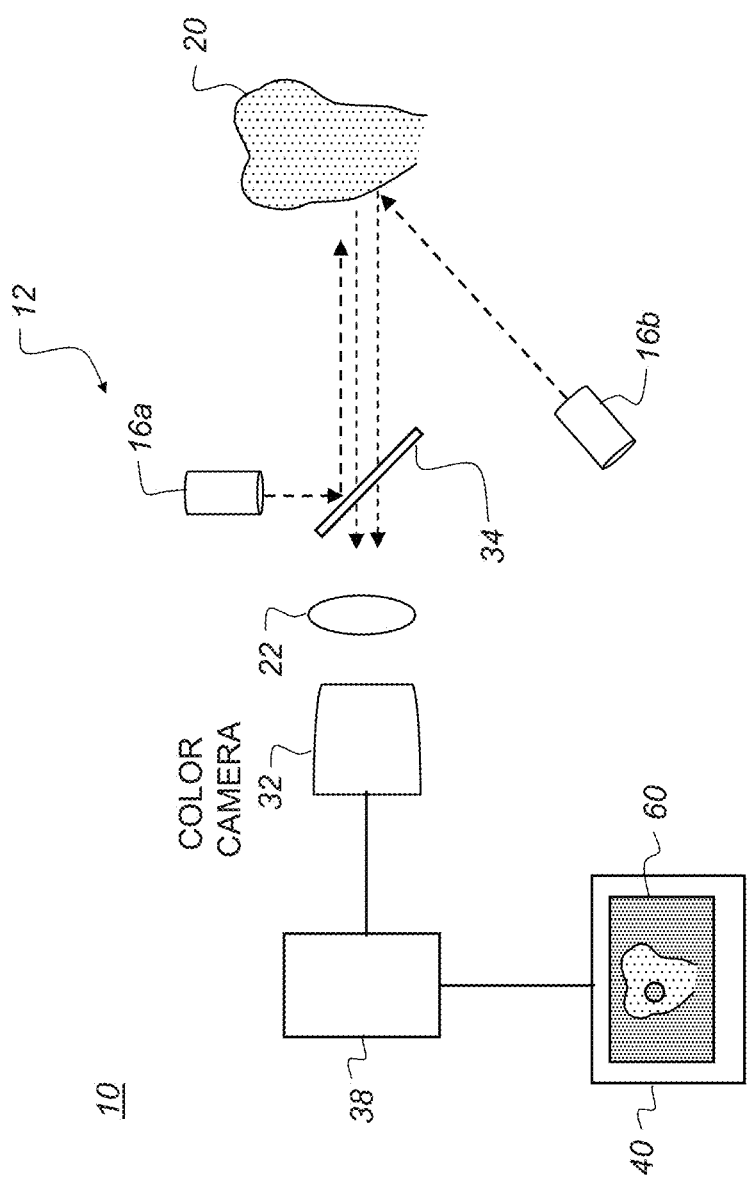
FIG. 8 is a schematic block diagram of an imaging apparatus for caries detection according to an alternate embodiment using multiple light sources.

For example, various types of light sources 12 could be used, with various different embodiments employing a camera or other type of image sensor. While a single light source 12 could be used for fluorescence excitation, it may be beneficial to apply light from multiple incident light sources 12 for obtaining multiple images. Referring to the alternate embodiment of FIG. 8, light source 12 might be a more complex assembly that includes one light source 16a for providing light of appropriate energy level and wavelength for exciting fluorescent emission and another light source 16b for providing illumination at different times. The additional light source 16b could provide light at wavelength and energy levels best suited for back-scattered reflectance imaging. Or, it could provide white light illumination, or other polychromatic illumination, for capturing a white light image or polychromatic image which, when displayed side-by-side with a FIRE image, can help to identify features that might otherwise confound caries detection, such as stains or hypocalcification. The white light image itself might also provide the back-scattered reflectance data that is used with the fluorescence data for generating the FIRE image. Supporting optics for both illumination and image-bearing light paths could have any number of forms. A variety of support components could be fitted about the tooth and used by the dentist or dental technician who obtains the images. Such components might be used, for example, to appropriately position the light source or sensing elements or to ease patient discomfort during imaging.

Thus, what is provided is an apparatus and method for caries detection at early and at later stages using combined effects of back-scattered reflectance and fluorescence.

PARTS LIST 10 imaging apparatus
12 light source
13 diffuser
14 lens
16a light source
16b light source
18 polarizing beamsplitter
20 tooth
22 lens
26 filter
28 filter
30 camera
32 camera
34 beamsplitter
38 processing apparatus
40 display
42 polarizer
44 analyzer
50 fluorescence image
52 reflectance image
54 white-light image
58 carious region
60 FIRE image
62 threshold image
64 enhanced threshold FIRE image

The invention claimed is:

1. A method for calibrating an imaging apparatus for teeth comprising:
    (a) obtaining a spectral measurement from at least one light source;
    (b) obtaining a spectral measurement from a fluorescent emission generated from a tooth in response to said at least one light source;
    (c) measuring the spectral response of a camera; and
    (d) generating scalar multiplier values to be used in image processing, according to the spectral measurements made in steps (a), (b), and (c), where the image processing comprises,
        accessing fluorescence image data obtained from a fluorescent emission excited by incident light directed toward a tooth,
        multiplying the fluorescence image data value by a first scalar multiplier according to the spectral measurements made in steps (b) and (c) to form a first value,
        accessing back-scattered reflectance image data from the tooth tissue obtained from back-scattered light,
        multiplying the back-scattered image data value by a second scalar multiplier according to the spectral measurements made in steps (a) and (c) to form a second value,
        adjusting the multiplied fluorescence image data with the multiplied back-scattered reflectance image data to form an enhanced image of the tooth tissue.

2. The method of claim 1, further comprising storing, transmitting, or displaying the scalar multiplier values.

3. The method of claim 1, further comprising:
    processing an image using the scalar multiplier values; and
    displaying the processed image.

4. The method of claim 1 further comprising displaying, storing, or transmitting the enhanced image of the tooth tissue.

5. The method of claim 1, wherein the camera is a color camera, wherein the fluorescence image data and back-scattered reflectance image data are obtained from different color planes of a single, full-color image capture.

6. The method of claim 1, comprising:
    directing incident light toward the tooth;
    obtaining fluorescence image data from a fluorescent emission excited by the incident light; and
    obtaining, from back-scattered light, back-scattered reflectance image data from tooth tissue.

7. The method of claim 6, wherein the obtaining steps are performed simultaneously.

8. The method of claim 6 wherein directing incident light comprises energizing at least two light sources.

9. The method of claim 8, wherein the at least two light sources are energized over different time intervals.

10. The method of claim 1, wherein the adjusting is a subtraction operation.

* * * * *